(12) United States Patent
Ullah et al.

(10) Patent No.: US 6,224,910 B1
(45) Date of Patent: May 1, 2001

(54) METHOD FOR THE PREPARATION OF AN ENTERIC COATED HIGH DRUG LOAD PHARMACEUTICAL COMPOSITION

(75) Inventors: Ismat Ullah, Cranbury; Gary J. Wiley, Jackson, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/408,098

(22) Filed: Sep. 29, 1999

Related U.S. Application Data

(62) Division of application No. 09/083,597, filed on May 22, 1998, now abandoned.

(51) Int. Cl.[7] .............. A61K 9/48; A61K 9/64; A61K 9/14; A61K 9/16
(52) U.S. Cl. .......... 424/489; 424/451; 424/456; 424/490; 424/494; 424/497
(58) Field of Search .................. 424/458, 460, 424/462, 463, 471, 489

(56) References Cited

U.S. PATENT DOCUMENTS

| | | | |
|---|---|---|---|
| 4,432,966 | 2/1984 | Zeitoun et al. | 424/21 |
| 4,524,060 | 6/1985 | Mughal et al. | 424/19 |
| 4,556,552 | 12/1985 | Porter et al. | 424/32 |
| 4,704,295 | 11/1987 | Porter et al. | 424/3 |
| 4,775,536 | 10/1988 | Patell | 424/471 |
| 4,786,505 | 11/1988 | Lovgren et al. | 424/468 |
| 4,794,001 | 12/1988 | Mehta et al. | 424/458 |
| 4,808,413 | 2/1989 | Joshi et al. | 424/458 |
| 4,853,230 | 8/1989 | Lovgren et al. | 424/466 |
| 4,861,759 | 8/1989 | Mitsuya et al. | 514/46 |
| 4,925,675 | 5/1990 | Giannini et al. | 424/469 |
| 4,975,283 | 12/1990 | Patell | 424/470 |
| 4,994,279 | 2/1991 | Aoki et al. | 424/494 |
| 5,026,559 | 6/1991 | Eichel et al. | 424/458 |
| 5,026,560 | 6/1991 | Makino et al. | 424/494 |
| 5,158,777 | * 10/1992 | Abramowitz et al. | 424/458 |
| 5,175,003 | 12/1992 | Goldman . | |
| 5,225,202 | * 7/1993 | Hodges et al. | 424/480 |
| 5,254,539 | 10/1993 | Mitsuya et al. | 514/46 |
| 5,350,584 | 9/1994 | McClelland et al. | 424/501 |
| 5,536,507 | 7/1996 | Abramowitz et al. | 424/479 |
| 5,616,566 | 4/1997 | Mitsuya et al. | 514/47 |
| 5,686,106 | 11/1997 | Kelm et al. | 424/463 |
| 5,733,575 | 3/1998 | Mehra et al. | 424/480 |

FOREIGN PATENT DOCUMENTS

| | | | |
|---|---|---|---|
| 0754452 | 1/1997 | (EP) | A61K/9/52 |
| 0781549 | 7/1997 | (EP) | A61K/9/28 |
| 94/03160 | 2/1994 | (WO) . | |

OTHER PUBLICATIONS

Ishibashi et al., "Design and Evaluation of a New Capsule–Type Dosage Form for Colon–Targeted Delivery of Drugs", Int'l J. of Pharmaceutics 168 (1998) pp. 31–40.

C.G. Wilson and Neena Washington, "Small Intestine: Transit and Absorption of Drugs"; Chapter 5—Physiological Pharmaceutics—Biological Barriers to Drug Absorption; 1989 pp. 71–90.

* cited by examiner

Primary Examiner—Thurman K. Page
Assistant Examiner—S. Tran
(74) Attorney, Agent, or Firm—Gabriel Lopez; David M. Morse

(57) ABSTRACT

A high drug load enteric coated pharmaceutical composition is provided which includes a core comprised of a medicament which is sensitive to a low pH environment of less than 3, such as ddI, which composition is preferably in the form of beadlets having an enteric coating formed of methacrylic acid copolymer, plasticizer and an additional coat comprising an anti-adherent. The so-called beadlets have excellent resistance to disintegration at pH less than 3 but have excellent drug release properties at pH greater than 4.5. A novel method of making said pharmaceutical composition is also disclosed.

45 Claims, 1 Drawing Sheet

METHOD FOR THE PREPARATION OF AN ENTERIC COATED HIGH DRUG LOAD PHARMACEUTICAL COMPOSITION

This application is a divisional of U.S. application Ser. No. 09/083,597, filed May 22, 1998, abandoned.

BRIEF DESCRIPTION OF THE INVENTION

The present invention is directed to an enteric-coated pharmaceutical composition comprising an acid labile high drug load medicament which is sensitive to a low pH environment of less than 3, such as ddI, which composition is also in the form of beadlets or tablets which includes an enteric coating such as Eudragit L-30-D 55 and a plasticizer, but does not require a subcoat; the beadlets also having an anti-adherent coat. The so-called beadlets have excellent resistance to disintegration at pH less than 3 but have excellent drug release properties at pH greater than 4.5. A novel method of making said pharmaceutical composition is also disclosed.

BACKGROUND OF THE INVENTION

Enteric coatings have been used for many years to arrest the release of the drug from orally ingestible dosage forms. Depending upon the composition and/or thickness, the enteric coatings are resistant to stomach acid for required periods of time before they begin to disintegrate and permit slow release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64–71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001).

Most enteric coating polymers begin to become soluble at pH 5.5 and above, with maximum solubility rates at pHs greater than 6.5.

Numerous enteric coated and/or extended release pharmaceutical compositions and the methods of making these compositions have been disclosed in the art. Although some of these previously disclosed compositions are formed into small beadlets or pellets, they often comprise numerous extra ingredients in addition to the medicaments, such as fillers, buffering agents, binders and wetting agents, all of which add to the bulk of the composition and reduce the amount of active medicament which can be contained in the composition. The processes of preparing these aforementioned pharmaceutical compositions require multiple time consuming steps, including subcoating and outer coating steps. Furthermore, many of these pharmaceutical compositions are intended for delivery in the lower GI tract, i.e. in the colon, as opposed to the upper intestines, i.e. the duodenum of the small intestine.

U.S. Pat. No. 5,225,202 discloses enteric coated pharmaceutical compositions utilizing neutralized hydroxypropyl methylcellulose phthalate polymer (HPMCP) coating. The pharmaceutical compositions disclosed comprise an acid labile medicament core, a disintegrant, one or more buffering agents to provide added gastric protection in addition to the enteric coating, as well as the enteric coating and a plasticizer. The pharmaceutical composition may also include one or more lactose, sugar or starch fillers. According to the invention disclosed in this reference, when the core includes a drug which is incompatible with the enteric coating layer, an additional subcoat layer which acts as a physical barrier between the core and outer enteric coating layer is employed to prevent interaction of the acid labile drug and the acidic enteric coat. The HPMCP enteric coating starts its dissolution process at pH 5.0. The process of preparing this pharmaceutical composition requires numerous coating steps to apply the subcoat and then the enteric coat.

U.S. Pat. No. 5,026,560 discloses a pharmaceutical composition and method of making said pharmaceutical composition, wherein the pharmaceutical composition comprises a Nonpareil seed core produced by coating sucrose with corn starch, spraying the core with an aqueous binder in a solution of water or ethanol and with a spraying powder containing a drug and low substituted hydroxypropylcellulose, followed by the application of an enteric coating.

U.S. Pat. No. 4,524,060 recites a slow release pharmaceutical composition which provides a sustained release composition for treating hypertensive patients, and which comprises a mixture of micronized indoramin or a pharmaceutically acceptable salt thereof, a water-channeling agent, a wetting agent, a disintegrant, the mixture being in the form of a non-compressed pellet and having an enteric coat or sustained release coat permeable to gastrointestinal juices.

U.S. Pat. No. 5,536,507 is directed to a pharmaceutical composition having a delayed release coating or enteric coatings wherein the active agent in the composition is intended for release of a predominant amount of the drug at a point near the inlet to or within the large intestine and at a pH of approximately 6.4–7.0.

Pharmaceutical compositions which include a medicament which is unstable in an acidic environment such as the stomach and which is not adequately buffered, will require an enteric protective coating to prevent release of such medicament prior to reaching the intestines.

ddI, (also known as didanosine or 2',3'-dideoxyinosine, and marketed by Bristol-Myers Squibb Co. under the brand name Videx®), is an acid labile drug which has the formula

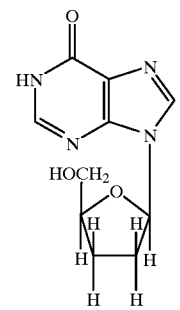

and which has been shown to be effective in the treatment of patients with the HIV virus which causes AIDS. The composition and method of inhibiting HIV replication with 2',3'-dideoxyinosine have been reported. See U.S. Pat. Nos. 4,861,759, 5,254,539 and 5,616,566, which are incorporated by reference herein. More recently, Videx® has become widely used as a component of the new therapeutic cocktails used to treat AIDS. It is also an acid labile medicament sensitive to a low pH environment and will degrade in the stomach.

Videx® is generally available in a variety of oral dosages, including Chewable/Dispersible Buffered Tablets in strengths of 25, 50, 100 or 150 mg of didanosine. Each tablet is buffered with calcium carbonate and magnesium hydroxide. Videx® tablets also contain aspartame, sorbitol, microcrystalline cellulose, Polyplasdone®, mandarin-orange flavor, and magnesium stearate. Videx® Buffered Powder for Oral Solution is supplied for oral administration in single-dose packets containing 100, 167 or 250 mg of didanosine. Packets of each product strength also contain a citrate-phosphate buffer (composed of dibasic sodium phosphate, sodium citrate, and citric acid) and sucrose. A Videx® Pediatric Powder for Oral Solution is also available and which is supplied for oral administration in 4- or 8-ounce glass bottles containing 2 or 4 grams of didanosine respectively, and is to be mixed with commercial antacid before oral ingestion.

With particular emphasis on the tablets, whether ingested alone or as part of a combination ("cocktail") therapy regimen, the current chewable/dispersible buffered tablets are not conducive from a patient ease of use standpoint. Whereas the other products which are a part of the AIDS therapeutic cocktail are capsules or tablets and easily swallowed, the Videx® (referred to herein as "ddl") Chewable/Dispersible Buffered Tablets must be thoroughly chewed, manually crushed, or uniformly dispersed in water before administration. Because ddl degrades rapidly at acidic pH, ddl, in its chewable/dispersible form and its buffered powder for oral solution, contains buffering agents and is administered with antacids in the pediatric powder form. However, the presence of the large quantities of antacid components in the formulation can lead to significant GI imbalance as noted by severe diarrhea. Many patients also complain about chewing the large ddl tablets (dose=2 tablets of 2.1 g each), the taste of the ddl or the time required to disperse the tablets and the volume of fluid (4 oz) required for the dose. All these factors, coupled with the fact that other nucleoside analog drugs are marketed in a more convenient dosage presentation (i.e. capsule or smaller tablets), necessitate the development of an innovative dosage form of ddl which is easy to swallow and does not cause discomforting side effects.

The current adult dose of 200 mg twice a day or possibly 400 mg daily would require very high drug load beads or particles so that the 400 mg dose could be encapsulated in a single capsule. A low drug load formulation would require multiple capsules/dose, which would be less convenient from a patient dosing point of view.

Accordingly, there is provided a coating which prevents release of the medicament in the stomach and allows for release of the drug in the small intestine thereby eliminating the need for an antacid which may cause GI imbalance upon chronic use. Thus, pharmaceutical compositions which include a medicament which is unstable in an acid environment such as the stomach will require such a protective coating to prevent release of such medicament prior to reaching the intestines.

DESCRIPTION OF THE INVENTION

Figure 1:
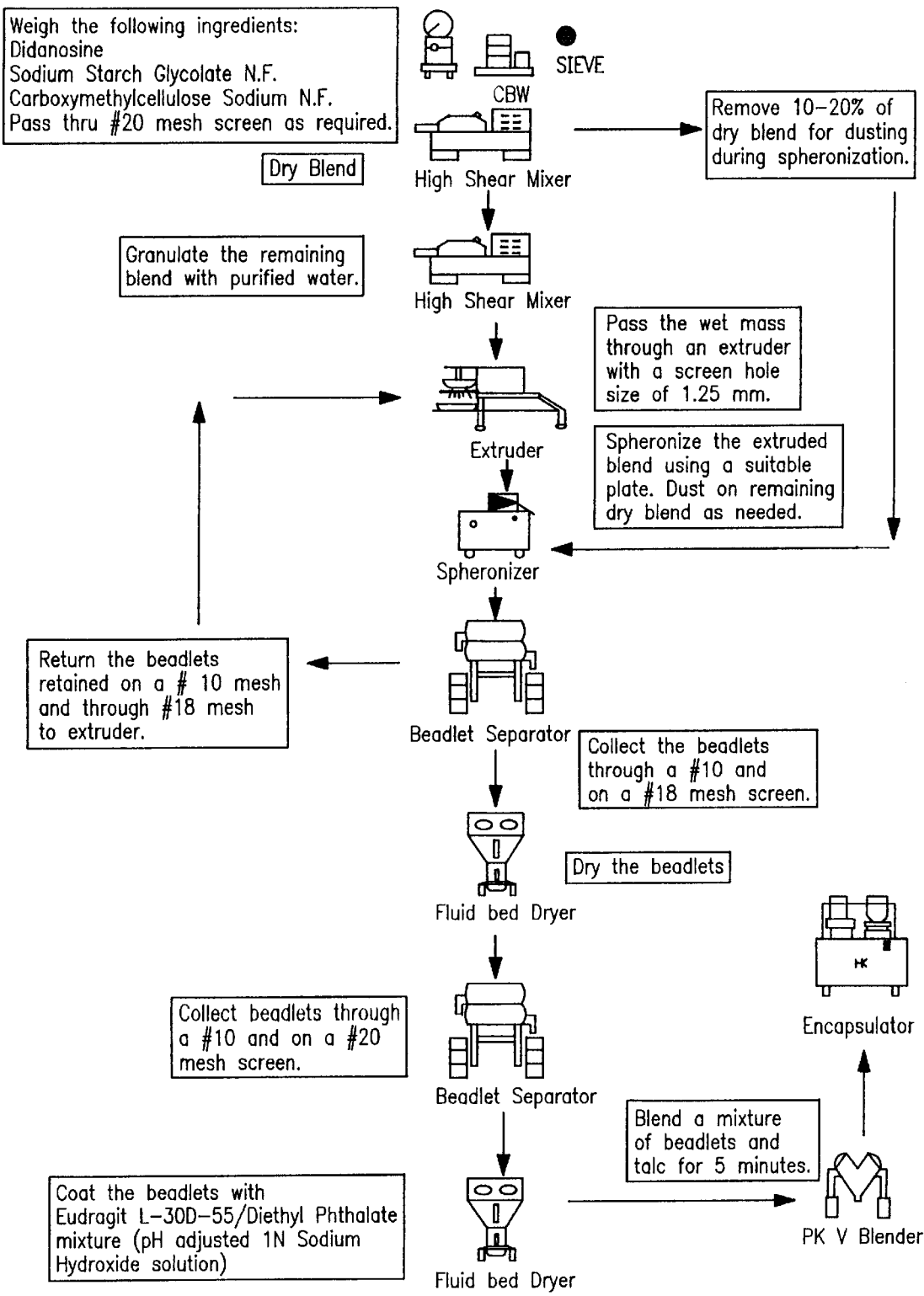
FIG. 1 is diagrammatic flow chart generally illustrating the process for manufacturing the enteric coated pharmaceutical composition of the present invention.

In accordance with the present invention, an enteric coated, high drug load pharmaceutical composition, and a method of making said pharmaceutical composition, is provided which includes a medicament which may degrade in a low pH environment but which is protected from doing so by the enteric coating. The pharmaceutical composition of the invention, which is advantageously in the form of beadlets, pellets or tablets, includes a core which comprises a medicament which is sensitive to a low pH environment, such as ddl, and optionally a binder, a disintegrant or swelling agent, and a filler. The core further comprises an enteric coating surrounding the core which includes a methacrylic acid copolymer and a plasticizer. The pharmaceutical composition may further comprise an anti-adherent coat.

The novel enteric coated pharmaceutical of the invention will provide for protection of the medicament or therapeutically active agent, such as ddl, at pH's less than 3 (such as found in the stomach) but will permit drug release at a pH of 4.5 or higher (such as found in the upper intestines).

Accordingly, the pharmaceutical composition of the invention will usually include drugs which are chemically unstable in acidic environments. The pharmaceutical composition of the invention provides excellent protection in very acidic environments (pH<3) while not delaying the rapid release in regions of pH greater than 4, whether this be the upper intestine or the duodenum.

Most of the enteric coating materials known in the art are acidic in nature and hence may cause chemical instability when in contact with acid labile ingredients. This is especially true under high temperature and humid conditions experienced during an aqueous coating process. To minimize this acid caused instability, a protective coat or subcoat is usually applied between the particles, beadlets, pellets, etc., and the enteric coat. This protective coat physically separates the acid labile drug from the acidic enteric coat, and hence improves stability of the formulation.

A process is thus described by which tablets, beadlets, pellets, and/or particles containing acid labile drugs can be successfully aqueous enteric coated without application of the protective coat or subcoat. This process involves raising the pH of the enteric coating suspension solution by using alkalizing agents. The pH of the coating suspension is raised below the point where enteric integrity of the polymer could be lost. The process may also involve the inclusion of binders, such as sodium carboxymethylcellulose, fillers, such as microcrystalline cellulose, disintegrants, such as sodium starch glycolate, and other excipients, such as magnesium oxide, which are relatively alkaline in nature, in the formulations intended for enteric coating. These steps provide a more stable composition for the acid labile drug in the core. As a result, incompatibility between the acid labile drug and the acidic enteric coating is reduced and there is no need for a protective subcoat between the acid labile drug and the acidic enteric coat. This process not only eliminates the costly additional subcoating step, but allows quicker release of the drug since the added subcoat layer delays drug release.

Normally, drug beads are formed by preparing a wet mass which is extruded into threads or noodles. These are spun on a high-speed rotating plate which breaks these into small pieces and rounds the ends to make spherical particles by a process known as spheronization. This spheronization generates centrifugal force. Under these forces, if the particles do not have enough moisture absorbent, the moisture will be extracted out of the particles (drawn to the surface), which will cause agglomeration. Microcrystalline cellulose is a good moisture absorbent and is thus an excellent spheronization aid. Often more than 15%, and usually more than 30%, is needed to obtain good spheronization characteristics.

It has been observed that when moisture is drawn to the surface during spheronization, dry powder could be dusted on the particles to quench the moisture and prevent agglomeration. It was believed by the inventors herein that this process could be used to completely eliminate the use of moisture absorbent in the formulation to prepare high drug load beads. It was further believed by the inventors that the drug with dry binder (if necessary) and optional disintegrant could be blended. A major portion of this dry blend could be wet massed, extruded, and the remaining dry blend used for quenching the moisture that surfaces during spheronization. This technique allows very high drug loads and would not change the composition of the bead, regardless of the amount of dry blend used for dusting.

The process of the present invention allows for formation of beads with very high drug load (up to 100%), and generally involves the preparation of a dry blend of powdered drug substance with or without a very small amount of suitable binder and optional disintegrant. The drug itself, the drug/dry binder mixture, or the drug/dry binder/disintegrant mixture should be capable of becoming tacky upon moistening. A major portion (70–95%) of this blend is wet massed, extruded and spheronized as is conventionally performed in the art for bead formation. A minor portion (5–30%) of the blend is set aside for dusting. As the spheronization process proceeds, extrudate strands break and the particles are rounded off. During this process, moisture is extracted out of these particles. The portion of the dry blend set aside earlier is dusted upon the moist particles to quench the surface moisture. This renders the particles relatively dry and free to move in a conventional rope formation pattern. Accordingly, spheronization of the beads progresses without agglomeration.

Often, enteric-coated or modified release beads or particles are prepared for oral delivery of the drugs in capsule dosage form. Upon oral ingestion the capsule shell dissolves allowing the contents in the capsule to be exposed to the gastric contents. Due to the presence of fluids in the stomach, exposed particles become moistened. If the moist particles do not stick together, they will disperse into the gastric contents and may begin to enter the duodenum based on the size distribution and other factors which control the gastric transit time. However, if the particles become tacky upon moistening, they may stick together as one or more lumps. In this case, such lumps may behave as large particles and their gastric emptying time will be variable depending upon the size and the strength of the lumps formed. In this case, such a dosage form would not behave as a true multiparticulate system. In order to solve this problem, according to the process of the present invention, enteric-coated beadlets, pellets, particles or tablets are over coated with a hydrophobic anti adherent before encapsulation. The amount of hydrophobic coating is kept to a level where it is just enough to prevent particle sticking after the capsule shell has dissolved, but not too much to retard dissolution. By this simple process, the particles behave as individual particles, and the gastric transit time is closer to that which is expected for the particle size for which the dosage form was designed, thus resulting in a more predictable and less variable dosage form.

The process of the present invention illustrates the preparation of high (up to 100%) potency (uncoated) beadlets, for acid labile drugs, such as ddI, using an aqueous process. No specialized equipment is required as conventional extrusion and spheronization equipment was found to be adequate for beadlet formation. Use of an alkaline binder, such as sodium carboxymethylcellulose, and dusting during spheronization with a dry blend mixture comprising the medicament, and optionally binder and a disintegrant, insured chemical stability of the medicament and maximized the drug load. The process of the present invention resulted in high (>90%) yield of beads of narrow particle size cut.

The invention is particularly adapted to pharmaceutical compositions such as beadlets, pellets or tablets, preferably beadlets, containing ddI as the medicament. ddI will be present in an amount of about up to 100% of the composition in the coated beadlets.

The coated beadlets pass through the stomach first. The transit time for the stomach is approximately two hours and the pH of this region is approximately 1 to 3. The enteric coating component allows the medicament core to remain substantially intact and thus prevents the pharmacologically active substance from being released in this region or the acid from penetrating through to the bead core. The beadlets then pass through the small intestine wherein the majority of the enteric coating component will dissolve and release the pharmacologically active substance therein. In normal flow direction therethrough, the small intestine consists of the duodenum, jejunum and ileum. Transit time through the small intestine is approximately 2–4 hours and the pH of these regions is approximately 5 to approximately 7.2.

As used herein "enteric coating", is a polymer material or materials which encases the medicament core. The polymeric enteric coating material in the present invention does not contain any active compound, i.e. any therapeutically active agent, of the present invention. Preferably, a substantial amount or all of the enteric polymer coating material is dissolved before the medicament or therapeutically active agent is released from the dosage form, so as to achieve delayed dissolution of the medicament core. A suitable pH-sensitive polymer is one which will dissolve with intestinal juices at the higher pH levels (pH greater than 4.5), such as within the small intestine and therefore permit release of the pharmacologically active substance in the regions of the small intestine and not in the upper portion of the GI tract, such as the stomach.

The polymer coating material is selected such that the therapeutically active agent will be released when the dosage form reaches the small intestine or a region in which the pH is greater than pH 4.5. Preferred coating pH-sensitive materials, which remain intact in the lower pH environs of the stomach, but which disintegrate or dissolve at the pH commonly found in the small intestine of the patient. The enteric polymer coating material begins to dissolve in an aqueous solution at pH between about 4.5 to about 5.5. The pH-solubility behavior of the enteric polymers of the present invention are such that significant dissolution of the enteric polymer coating will not occur until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours and permit reproducible release therein, the coating should begin to dissolve within the pH range of the duodenum and continue to dissolve at the pH range within the small intestine. Therefore, the amount of enteric polymer coating should be such that it is substantially dissolved during the approximate three hour transit time within the small intestine.

The pharmaceutical medicament present in the core will be an acid labile drug such as ddI, pravastatin, erythromycin, digoxin, pancreatin, ddA (2',3'-dideoxyadenosine), ddC (2', 3'-didexoycytosine), and the like. The present invention is not limited to these drugs and other drugs may be used as well.

One or more binders may be present in the core in an amount within the range of from about 0 to about 10% and preferably about 1% by weight of the composition. Sodium carboxymethylcellulose is the preferred binder most suitable for use herein. Examples of other binders which may be used include Avicel™ PH101, Avicel™ RC 591, Avicel™ CL-61 1, (FMC Corp), Methocel™ E-5 (Dow Corp.), Starch 1500 (Colorcon, Ltd.), Hydroxypropyl Methylcellulose (HPMC) (Shin-Etsu Chemical Co., Ltd.), Polyvinylpyrrolidone, Potassium Alginate and Sodium Alginate.

The core of the composition of the invention may also include one or more disintegrants or swelling agents in an amount within the range from about 1% to about 4% by weight of the composition, such as sodium starch glycolate marketed under the trademark EXPLOTAB (Edward Mendell Co.), Ac-Di-Sol (cross-linked sodium carboxymethylcellulose) (FMC Corp), croscarmellose sodium, corn starch, or cross linked polyvinylpyrrolidone.

The core employed in the pharmaceutical composition of the invention may be formed of a beadlet or pellet having a diameter of from about 0.5 to about 5 mm, and preferably from about 1 to about 2 mm. The core will preferably be in the form of a beadlet or a pellet.

In forming the enteric coated pharmaceutical composition of the invention, an enteric coating solution of Eudragit L-30-D 55 will be employed. Eudragit L-30-D 55 is an aqueous acrylic resin dispersion, an anionic copolymer derived from methacrylic acid and ethyl acrylate with a ratio of free carboxyl groups to the ester of approximately 1:1, and a mean molecular weight of approximately 250,000, is supplied as an aqueous dispersion containing 30% w/w of dry lacquer substance, and is marketed by Rohm-Pharma Co., Germany. As an aqueous-based coating, no dangerous or environmentally harmful organic solvents are utilized.

Although Eudragit is the preferred coating polymer, the invention is not limited in this respect and other enteric coating polymers known in the art, such as hydroxypropyl methylcellulose phthalate HP50 (HPMCP-HP50) (USP/NF 220824), HP55 (HPMCP-HP55) (USP/NF type 200731) and HP55S available from Shin Etsu Chemical, Coateric™ (polyvinyl acetate phthalate) (Colorcon Ltd.), Sureteric™ (polyvinyl acetate phthalate) (Colorcon, Ltd.), or Aquateric™ (cellulose acetate phthalate) (FMC Corp.) and the like may be employed.

The enteric coating will also preferably contain a plasticizer which is preferably diethyl phthalate, although the invention is not limited in this respect and other plasticizers may be used such as triethyl citrate (Citroflex-2), triacetin, tributyl sebecate, or polyethylene glycol. Optionally an anti-adherent (anti-agglomerant) which is advantageously a hydrophobic material such as talc, magnesium stearate or fumed silica, with talc being referred, can be applied after coating the beadlet or pellet.

The enteric coating employed is substantially easier to process than previously reported coating systems, and is especially advantageous for coating small diameter, low mass particles (beadlets) with minimal processing problems (agglomeration) without the need for organic solvents.

The above enteric coating will include methacrylic acid copolymer in an amount of approximately 5%–30%, and preferably 10%–20% by weight based on solids content of the enteric coating solution, and plasticizer in an amount of approximately 5%–6%, and preferably 2%–3% by weight.

All of the above weights are based on total concentration of solids in the enteric coating solution/suspension.

The enteric coating will thus contain from about 5% to about 35% by weight of solids, and from about 65% to about 95% by weight of water.

In general, where the core includes a drug which is incompatible with the enteric coating layer, a subcoat layer which may be comprised of one or more film-formers or plasticizers, and which acts as a physical barrier between the core and the outer enteric coating layer will be employed. However, unlike previously reported coatings such as that disclosed in U.S. Pat. No. 5,225,202, the novel pharmaceutical composition of the invention, as a result of the novel process utilized in making the composition of the present invention and the pH adjustment of the coating, does not require a subcoat since the need for such an insulating layer is eliminated by stabilizing the beadlets with an alkalizing agent and by aqueous coating at pH 5. Since the coating is designed to breakdown at pH 5.5, the enteric coating applied at pH 5 permits relatively rapid breakdown in the intestine as only a small amount of additional alkalinity is required to bring the pH to 5.5.

The enteric coating will be present in a weight ratio to the core of within the range of from about 5% to about 30% for release in the small intestine, but may be increased to approximately 60% for release in the colon.

A preferred enteric coated beadlet formulation is set out below.

| Material | Possible Range % | Preferred Composition Total % |
| --- | --- | --- |
| CORE | | |
| Drug (didanosine) | 50–100.0 | 95.00 |
| NaCMC | 0–10.0 | 1.00 |
| Na Starch Glycolate | 0–10.0 | 4.00 |
| COATING | | |
| Eudragit L-30-D 55 | 5.0–30.0 | 10–20 |
| Diethyl Phthalate | 0.5–6.0 | 1.5–3.0 |
| ANTI-ADHERENT | | |
| Talc | 0.1–4.0 | 0.2–0.5 |

The enteric coated pharmaceutical composition in the form of beadlets or pellets may be prepared by a process which comprises the steps of first preparing uncoated beadlets by preparing a dry blend comprised of an acid labile medicament, a binder, such as NaCMC, and a disintegrant, such as sodium starch glycolate, using a tumbling type blender, a planetary mixer, or a high shear mixer. A portion in an amount from about 5%–30%, and preferably 10%–20%, of the dried blend is set aside for later dusting during spheronization. Water is then added to the remaining 70%–95% of dry blend and granulated to a suitable wet granulation mass using a planetary or high shear mixer. The wet mass is extruded, for example, employing a Nica or other type extruder to form an extrudate which is then placed in a spheronizer such as Caleva, Nica or other type to form wet beadlets which are dusted during spheronization with the 5%–30% of dry blend previously set aside. The beadlets are then sized through mesh screens to obtain the desired beadlet sizes. The beadlets may then be dried by tray drying or by fluid bed drying. The general process of the present invention using ddI as the acid labile medicament is diagrammatically illustrated in FIG. 1.

The dried beadlets or pellets may then be coated with an enteric film coating suspension comprising Eudragit L-30-D and plasticizer (diethyl phthalate), using a fluid bed coater, such as a Wurster spray coating system or other suitable coating system, and then dried. During preparation of the film coating suspension, a NaOH solution is added to the suspension until a pH of 5.0±0.1 is obtained. Stabilization of the beadlets with a binder and the adjustment of the enteric film coating suspension to pH 5 eliminates the need for a subcoat or insulating layer. The advantage here is that an enteric coating at pH 5 permits relatively rapid breakdown in the intestine since only a small amount of alkalinity is required to bring the pH to 5.5.

To prevent clumping of the film coated beads, a hydrophobic anti-adherent (talc) is then added to the film coated beads and blended.

The so-formed beadlets or pellets may then be filled into hard shell capsules, such as gelatin capsules of varying sizes depending on the dosage of medicament desired.

The Examples represent preferred embodiments of the present invention. The following examples further describe the materials and methods used in carrying out the invention and are intended to be for illustrative purposes only, and are not intended to limit the scope or spirit of this invention or the claims in any way. All temperatures are expressed in degrees Centigrade unless otherwise indicated and all mesh sizes are U.S. standard ASTM.

EXAMPLE 1

A ddI formulation in the form of enteric-coated beadlets having the following composition was prepared as described below.

| COMPOSITION | WEIGHT % OF COMPONENT | WEIGHT % OF FINAL FORMULATION |
| --- | --- | --- |
| A: PELLET CORE | | |
| ddI | 95 | 77.744 |
| Na CMC | 1 | 0.818 |
| Na Starch Glycolate | 4 | 3.273 |
| B: COATING | | |
| Eudragit L-30-D 55 (dry basis) | 87 | 15.621 |
| Diethyl Phthalate | 13 | 2.343 |
| (pH adjustment to 5.0 ± 0.1) | | |
| C: ANTI-ADHERENT | | |
| Talc | 100 | 0.200 |
| D: CAPSULE | | |
| Size 0 clear body and cap | | |

The preparation of ddI beadlets commenced with the screening and blending of a mixture of ddI, sodium starch glycolate, and sodium carboxymethylcellulose. The resulting blend was then screened again and re-blended. Approximately 10%–20% of the second blend was then removed and set aside for dusting during spheronization. The remaining blend was then granulated to a suitable wet mass endpoint using a planetary mixer or high shear mixer. Approximately 200–360 g of water per 1 kg of dry blend was added while mixing until a suitable wet mass was achieved for extrusion. The wet mass was extruded through a suitable screen using an extruder (Nica Model E140, Feeder Speed 1, Agitator Speed 1), which achieved approximately 10/18 mesh fraction beads upon spheronization. The extrudate was transferred to a suitable spheronizer (Caleva Model 15 at 500 rpm, or Q-400 Marumerizer™ at 700 rpm), and spheronized at medium speed using a medium cross-hatch plate or a radial design plate for approximately 1–5 minutes. The 10%–20% of the previously prepared dry blend which was set aside was then used to dust the beads to prevent agglomeration. After the appropriate spheronization time, the product was discharged into an appropriate container.

The spheronized wet beads were then gently passed through #10 and #18 size mesh screens to collect 10/18 mesh product fraction. The over 10 and under 18 sized mesh fractions were returned to the extruder for re-extrusion and re-spheronization. This process was continued until at least 90% of the product fraction was obtained. The 10/18 mesh product fraction was then dried using a hot air tray dryer or a fluid bed type dryer to a predetermined pre-specified moisture content. The dried beads were screened through #10 and #20 mesh screens to remove any lumps or undersized beads. The 10/20 mesh product fraction dried beads were transferred to a suitable container lined with two polyethylene bags. The net weight was determined, and the % yield and accountability of the bead manufacturing process was calculated.

To prepare sufficient quantities of film coating suspension to coat the bead batch, Eudragit L-30-D 55 was filtered through a #60 mesh screen to remove any lumps present therein. The filtered Eudragit was weighed and then added with stirring to a tarred vessel containing one-half the amount of water required. The mixture was continuously stirred for 5 minutes or until a uniform mixture was visually evident. With continuous stirring, diethyl phthalate was added to the vessel and stirring continued for 20 minutes or until a uniform mixture was visually evident. A pH meter was then standardized using pH 4 and pH 7 buffers. With continued stirring, a NaOH solution was added to the vessel until a pH of 5.0±0.1 was obtained. The formula weight of the coating suspension was adjusted using water and stirring was continued for an additional 10 minutes.

In the bead coating procedure, a fluid bed processor was set up for a Wurster spray coating system or other suitable coating system. The ideal parameters for the spray coating system include an Aeromatic STREA-1, 300 g charge, 0.8 mm tip, 8 g/min spray rate, spray pressure 1.0 bar, inlet temp. 64° C., outlet temp. 42° C.; Glatt GPCG-5 with Wurster column, 1500 g, 1.2 mm tip, 20 g/min spray rate, spray pressure 1.0 bar, inlet temp 65° C., product temp. 48° C., outlet temp. 42° C.

Before commencing application of the film coating suspension, the beads may optionally be pre-heated to approximately 50° C. for approximately 5 min. A 16%–20% w/w film coating was applied using the previously described coating parameters. After film coating was completed the inlet temperature was reduced to maintain a product temperature of approximately 50° C. and the beads were then dried for 25±10 minutes. The net weight of the film coated beads was determined. The percentage of the film coating to the beads was calculated. The weight of the talc to add based on the net weight of the beads was determined. Actual % gain due to the film coat depends on the efficiency of the coating operation. The amount of coating applied can be adjusted to achieve the target weight gain due to coating. The determined weight of talc was then weighed out. The film coated beads were placed in a suitable tumbling type blender with the talc and blend for 15±5 minutes. The beads were then transferred to a suitable container(s) lined with two polyethylene bags and the net weight was determined.

The so-formed beadlets may then be filled into capsules or shells, such as gelatin capsules for ease of swallowing.

The so formed enteric coated ddl product was found to give excellent protection against gastric acid (at pH of 3) but had excellent release of ddl at pH's above 5.

EXAMPLE 2

A preferred ddl formulation in the form of enteric coated beadlets was prepared as described below. ddl (0.7774 kg), sodium starch glycolate (0.0327 kg) and NaCMC (0.0082 kg) were placed into a suitable blender/mixer. If a tumbling type blender was used, the mixture was blended for 10±2 min. If a planetary mixer was used, the mixture was mixed for 10±2 min. If a high shear mixer was used, the mixture was mixed for 5±2 min. If a tumbling type blender or planetary type mixer was used, the blend was milled through a Fitzmill equipped with hammers forward, #1 plate, and set at medium speed. This milled material was then placed into a tumbling type blender or planetary mixer and blended for 10±2 min. Prior to blending, if any of the ingredients required delumping, they were passed through a #20 mesh stainless steel screen.

Approximately 10%–20% of the second blend was then removed and set aside for dusting during spheronization. The remaining blend was then granulated to a suitable wet mass endpoint using a planetary mixer or high shear mixer. Approximately 200–360 g of water per 1 kg of dry blend was added while mixing until a suitable wet mass was achieved for extrusion. The wet mass was extruded through a suitable screen using a Nica Model E140, Feeder Speed 1, Agitator Speed 1 extruder which achieved a 10/18 mesh fraction bead upon spheronization. The extrudate was transferred to a suitable spheronizer, either a Caleva Model 15 at 500 rpm, or Q-400 Marumerizer™ at 700 rpm, and spheronized at medium speed using a medium cross-hatch plate (0.3 mm–0.4 mm) or a radial design plate for approximately 1–3 minutes. The 10%–20% of the previously prepared dry blend which was set aside was then used to dust the beads to prevent agglomeration. After the appropriate spheronization time, the product was discharged into an appropriate container.

The spheronized wet beads were then gently passed through #10 and #18 size mesh screens to collect 10/18 mesh product fraction. The over 10 and under 18 sized mesh fractions were returned to the extruder for re-extrusion and spheronization. This process was continued until at least 90% of the product fraction was obtained. The 10/18 mesh product fraction was then dried using a hot air tray dryer or a fluid bed type dryer set at 55° C. to 60° C. (e.g. Glatt GPC-5, Inlet temp. 60° C., Product temp. 50° C., Outlet temp. 42° C.) to achieve a predetermined pre-specified moisture content. The dried beads were screened through #10 and #20 mesh screens to remove any lumps or undersized beads. The 10/20 mesh product fraction dried beads were transferred to a suitable container lined with two polyethylene bags. The net weight was determined, and the % yield and accountability of the bead manufacturing process was calculated.

To prepare sufficient quantities of film coating to coat 1 kg of the bead batch, the solids quantities of Eudragit deposited on 1 kg of beads was 0.1562 kg. The quantities of diethyl phthalate deposited on 1 kg of beads was 0.0234 kg. The Eudragit L-30-D 55 was filtered through a #60 mesh screen to remove any lumps present therein. The filtered Eudragit (0.1562 kg, dry weight) was then added with stirring to a tarred vessel containing one-half the amount of water required. The mixture was continuously stirred for 5 minutes or until a uniform mixture was visually evident. With continuous stirring, diethyl phthalate (0.0234 kg) was added to the vessel and stirring continued for 20 minutes or until a uniform mixture is visually evident. A pH meter was then standardized using pH 4 and pH 7 buffers. With continued stirring, a NaOH solution is added to the vessel until a pH of 5.0±0.1 is obtained. The formula weight of the coating suspension is adjusted using water and stirring is continued for an additional 10 minutes.

The beadlets were then coated using a Wurster spray coating system. Ideal parameters for the spray coating system included an Aeromatic STREA-1, 300 g charge, 0.8 mm tip, 8 g/min spray rate, spray pressure 1.4 bar, inlet temp. 64° C., outlet temp. 42° C.; Glatt GPCG-5 with Wurster column, 1500 g, 1.2 mm tip, 20 g/min. spray rate, spray pressure 1.0 bar, inlet temp 65° C., product temp. 48° C., outlet temp. 42° C.

Before commencing application of the film coating suspension, the beads may optionally be pre-heated to approximately 50° C. for approximately 5 min and dried for 25±10 minutes. A 16%–20% w/w film coating using the previously established coating parameters was applied. After film coating is complete the inlet temperature was reduced to maintain a product temperature of approximately 50° C. and the beads were then dried for 25±10 minutes. The net weight of the film coated beads was determined. The percentage of the film coating to the beads was calculated.

The weight of the talc (at 0.2% level) to add based on the net weight of the beads was determined. The determined weight of talc was then weighed out. The film coated beads were placed in a suitable tumbling type blender with the talc and blended for 15±5 minutes. The beads were then transferred to a suitable container(s) lined with two polyethylene bags and the net weight was determined.

The so formed beadlets may then be filled in to capsules or shells, such as gelatin capsules for ease of swallowing.

The so formed enteric coated ddl product was found to gave excellent protection against gastric acid (at pH of 3) but had excellent release of ddl at pH's above 4.5.

We claim:

1. A process for the preparation of a high drug load enteric-coated pharmaceutical composition comprising the steps of:
    (a) preparing a dry blend comprising a medicament, a binder, and a disintegrant, and setting a portion of said dry blend aside;
    (b) forming a wet mass from the remainder of said dry blend not set aside in step (a);
    (c) extruding said wet mass to form an extrudate and spheronizing said extrudate into high-potency beadlets by dusting said wet mass extrudate with said portion of said dry blend set aside in step (a);
    (d) coating said beadlets with an enteric coating polymer and plasticizer in an aqueous media; and
    (e) blending said coated beadlets with an anti-adherent, wherein the process further comprising the step of separating said spheronized high potency beadlets formed in step ⓒ into 10/18 mesh sized beadlets prior to said coating step (d).

2. The process of claim 1, wherein said medicament is an acid labile drug.

3. The process of claim 2, wherein said acid labile drug is selected from the group consisting of ddl, pravastatin, erythromycin, digoxin, pancreatin, ddA, and ddC.

4. The process of claim 3, wherein said medicament is ddl.

5. The process of claim 1, wherein said binder is sodium carboxymethylcellulose.

6. The process of claim 1, wherein said disintegrant is sodium starch glycolate.

7. The process of claim 1, wherein the wet mass is formed by the addition of a granulation solvent.

8. The process of claim 7, wherein said granulation solvent is water.

9. The process of claim 1, wherein said plasticizer is diethyl phthalate.

10. The process of claim 9, wherein said enteric coating comprises methacrylic acid copolymer and diethyl phthalate.

11. The process of claim 10, wherein said copolymer is methacrylic acid copolymer, Type C.

12. The process of claim 1, wherein said anti-adherent is talc.

13. The process of claim 1, further comprising the step of filling said coated beadlets prepared in step (e) into a capsule.

14. The process of claim 13, wherein said capsule is a size 0 gelatin capsule.

15. The process of claim 14, wherein the beadlets in said capsule comprise 400 mg ddl.

16. A process for the preparation of enteric-coated 2',3'-dideoxyinosine (ddl) beadlets comprising the steps of:

(a) preparing a dry blend comprising ddl, a binder, and a disintegrant, and setting a portion of said dry blend aside;

(b) forming a wet mass from the remainder of said dry blend not set aside in step (a);

(c) extruding said wet mass to form an extrudate and spheronizing said extrudate into high-potency beadlets by dusting said wet mass extrudate with said portion of said dry blend set aside in step (a);

(d) coating said beadlets with an enteric coating polymer and plasticizer in an aqueous media; and (e) blending said coated beadlets with an anti-adherent, wherein the process further comprising the step of separating said spheronized high potency beadlets formed in step (c) into 10/18 mesh sized beadlets prior to said coating step (d).

17. The process of claim 16, wherein said binder is sodium carboxymethylcellulose.

18. The process of claim 16, wherein said disintegrant is sodium starch glycolate.

19. The process of claim 16, wherein the wet mass is formed by the addition of a granulation solvent.

20. The process of claim 19, wherein said granulation solvent is water.

21. The process of claim 16, wherein said plasticizer is diethyl phthalate.

22. The process of claim 21, wherein said enteric coating comprises methacrylic acid copolymer and diethyl phthalate.

23. The process of claim 22, wherein said copolymer is methacrylic acid copolymer, Type C.

24. The process of claim 16, wherein said anti-adherent is talc.

25. The process of claim 16, further comprising the step of filling said coated beadlets prepared in step (e) into a dissolvable capsule.

26. The process of claim 25, wherein said capsule is a size 0 gelatin capsule.

27. The process of claim 26, wherein the beadlets in said capsule comprise 400 mg ddl.

28. A process for the preparation of a high drug load enteric-coated pharmaceutical composition comprising the steps of:

(a) preparing a dry blend comprising from about 80 to about 100% medicament; from 0 to about 10% binder; and from 0 to about 10% disintegrant, all % by weight, and setting a portion of said dry blend aside;

(b) forming a wet mass from the remainder of said dry blend not set aside in step (a);

(c) extruding said wet mass to form an extrudate and spheronizing said extrudate into high-potency beadlets by dusting said wet mass extrudate with said portion of said dry blend set aside in step (a);

(d) coating said beadlets with an enteric coating polymer and plasticizer in an aqueous media; and (e) blending said coated beadlets with an anti-adherent, wherein the process further comprising the step of separating said spheronized high potency beadlets formed in step (c) into 10/18 mesh sized beadlets prior to said coating step (d).

29. The process of claim 28 wherein the medicament comprises 2',3'-dideoxyinosine.

30. The process of claim 29 wherein the medicament comprises 95–100% ddl.

31. The process of claim 28, wherein said dry blend consists essentially of from about 80 to about 100% ddl, from 0 to about 10% binder, and from 0 to about 10% disintegrant.

32. The process of claim 31, wherein said dry blend consists essentially of about 95% ddl, about 1% sodium carboxymethylcellulose, and about 5% sodium starch glycolate.

33. The process of claim 28, wherein said binder is sodium carboxymethylcellulose.

34. The process of claim 28, wherein said disintegrant is sodium starch glycolate.

35. The process of claim 28, wherein the wet mass if formed by the addition of a granulation solvent.

36. The process of claim 34, wherein said granulation solvent is water.

37. The process of claim 28, wherein said plasticizer is diethyl phthalate.

38. The process of claim 36, wherein said enteric coating comprises methacrylic acid copolymer and diethyl phthalate.

39. The process of claim 37, wherein said copolymer is methacrylic acid copolymer, Type C.

40. The process of claim 28, wherein said anti-adherent is talc.

41. The process of claim 28, further comprising the step of filling said coated beadlets prepared in step (e) into a capsule.

42. The process of claim 40, wherein said capsule is a size 0 gelatin capsule.

43. The process of claim 41, wherein the beadlets in said capsule comprise 400 mg ddl.

44. The process of claim 1 further comprising the steps of drying the 10/18 mesh sized beadlets and then separating said dried beadlets into 10/20 mesh sized beadlets prior to said coating step (d).

45. The process of claim 28 further comprising the steps of drying the 10/18 mesh sized beadlets and then separating said dried beadlets into 10/20 mesh sized beadlets prior to said coating step (d).

* * * * *